United States Patent [19]
Afilani

[11] Patent Number: 6,011,476
[45] Date of Patent: Jan. 4, 2000

[54] METERING CIRCUIT TO DETECT DIELECTROKINETIC RESPONSE

[75] Inventor: Thomas Afilani, Jersey Shore, Pa.

[73] Assignee: DKL International, Inc., Wilmington, Del.

[21] Appl. No.: 08/917,223

[22] Filed: Aug. 25, 1997

Related U.S. Application Data

[63] Continuation-in-part of application No. 08/758,248, Nov. 27, 1996, Pat. No. 5,748,088, and a continuation-in-part of application No. 08/840,069, Apr. 24, 1997.

[51] Int. Cl.$^7$ .................................................. G08B 23/00
[52] U.S. Cl. ..................................... 340/573.1; 340/568.1; 340/561; 340/562; 324/71.1; 324/72; 324/452; 324/457
[58] Field of Search ............................ 340/573, 572, 340/568, 561, 562, 540, 541, 563–567, 564, 565, 573.1, 568.1; 307/116; 324/457, 452, 72, 71.1

[56] References Cited

U.S. PATENT DOCUMENTS

| | | |
|---|---|---|
| 3,771,152 | 11/1973 | Dettling et al. . |
| 4,138,641 | 2/1979 | Karlin et al. . |
| 4,621,258 | 11/1986 | Campman . |
| 5,019,804 | 5/1991 | Fraden . |
| 5,300,889 | 4/1994 | Bakhoum .............................. 324/457 |
| 5,353,332 | 10/1994 | Raith et al. . |
| 5,434,798 | 7/1995 | Madebrink et al. . |
| 5,436,955 | 7/1995 | Kaewell, Jr. et al. . |
| 5,471,359 | 11/1995 | Simpson et al. .......................... 361/93 |
| 5,526,489 | 6/1996 | Nilakantan et al. . |
| 5,541,978 | 7/1996 | Brunner et al. . |
| 5,544,163 | 8/1996 | Madonna . |
| 5,566,388 | 10/1996 | Brame et al. . |
| 5,584,049 | 12/1996 | Weaver, Jr. et al. . |
| 5,748,088 | 5/1998 | Afilani ................................. 340/573.1 |

FOREIGN PATENT DOCUMENTS

WO 98/24077  6/1998  WIPO .

OTHER PUBLICATIONS

Keiichi, M. "Detecting Circuit of Signal," Patent Abstracts of Japan, vol. 007, No. 278, (p. 242), Dec. 1983 & JP 58 154671 A (Sep. 1983).

Murray, D.W., "Physical Examination of the DKL Life-Guard™ Model 3," Oct. 1998, (pp. 1–53).

Murray, et al., "Double–Blind Evaluation of the DKL Life-Guard Model 2," Apr. 1998, (21 pages).

Moore, A.D., "Electrostatics and its Applications," Electrical & Computer Engineering Dept., University of Michigan, Ann Arbor, (4 pages).

Pohl, H.A., "Dielectrophoresis: The Behavior of Neutral Matter in Nonuniform Electric Fields," (7 pages).

The New Lexicon "Webster's Encyclopedic Dictionary" of the English Language, (definitions of "electrokinetics," "electrophoresis," "kinesis," and "kinetics"; (5 pages).

Voss, D., "New Physics' Finds a Haven at the Patent Office," Science, vol. 294 May 1999 (pp. 1252–1254).

PCT Notification of Transmittal of The International Preliminary Examination Report, International Application No. PCT/US98/17266, dated Jun. 8, 1999 (6 pgs.).

*Primary Examiner*—Nina Tong
*Attorney, Agent, or Firm*—Nixon & Vanderhye P.C.

[57] ABSTRACT

A current detector and metering circuit is provided for a dielectrokinesis detecting device. This device is particularly useful in the areas of locating obscured entities, such as human beings, animals, materials, or controlled substances. A current detector is attached to an antenna and detects when subtle changes in the dielectrokinesis occurs within an detection environment. The present current detector automatically zeros itself to ambient electric field values and then has a heightened sensitivity for changes in that electrical field caused by changes in the dielectrokinesis. The present invention can be used for detection of hidden entities or substance, for motion detection, for medical diagnostic detection, and other uses.

28 Claims, 1 Drawing Sheet

METERING CIRCUIT TO DETECT DIELECTROKINETIC RESPONSE

CROSS REFERENCE TO RELATED APPLICATIONS

The present invention is a continuation-in-part of U.S. patent application Ser. No. 08/758,248 to Afilani filed on Nov. 27, 1996, now issued as U.S. Pat. No. 5,748,088, the disclosure in which is incorporated herein by reference and is attached hereto as Appendix A. In addition, the present invention is a continuation-in-part of U.S. application Ser. No. 08/840,069, to Afilani, filed on Apr. 24, 1997, the disclosure in which is also incorporated herein by reference and is attached hereto as Appendix B.

FIELD OF THE INVENTION

The present invention relates to methods and apparatus for locating various entities by detecting dielectrokinesis response in the entity. In particular, the present invention relates to a method and apparatus for detecting and metering current indicators of the dielectrokinesis response.

BACKGROUND OF THE INVENTION

Humans, animals, organic objects and other entities generate an external electric field and gradients thereof which cause polarization, de-polarization and re-polarization phenomenon in cellular membranes. These phenomenon result in polarization states which can be detected by a detector device as described in U.S. patent application Ser. Nos. 08/758,248 and 08/840,649, attached hereto as Appendices A and B. The background information with respect to dielectrokinesis effects and how they can be detected is thoroughly discussed in those applications attached hereto and incorporated herein by reference and thus, for the sake of brevity, such a discussion is not repeated here.

The present invention relates to an improvement to the detector and metering circuitry associated with the inventions described in those applications. In particular the circuitry shown in, for example, FIG. 5 of U.S. application Ser. No. 08/758,248 (Appendix A) includes an antenna 102 upon which the forces associated with dielectrokinesis effects act. The antenna 102 is connected to an optimal low pass filter F1, which outputs to a current detection device (in FIG. 5 shown as JFETs J1, J2, and J3). After the current detection JFETs, the current continues into a current meter, M1, and an optional piezo buzzer P1. The current detectors (JFETs J1, J2 and J3), together with the meter M1 and piezo buzzer P1 are used to detect the subtle currents on the antenna 102 which are induced by the dielectrokinesis effects.

Thus, in accordance with the description of FIG. 5 of application Ser. No. 08/758,248, the operator employs an antenna to sense the dielectrokinesis effects associated with the presence of an entity to be detected and thereby creates a very low level current in association with that detection. The low level current detector in FIG. 5 takes the low level current induced on the antenna 102 and passes it through the low pass filter F1 and then to the gate of the respective JFETs. If the current exceeds the gate threshold of operation for the respective JFETs, the JFETs open to thereby complete a circuit powered by battery B1 and including meter M1 and piezo buzzer P1. In this way, current induced on antenna 102 will control the operation of meters M1 and piezo buzzer P1 in order to thereby detect dielectrokinesis effects in the vicinity of the antenna 102 and display them (via meter M1 and piezo buzzer P1) to the operator.

The present invention is a circuit which is designed specifically to improve detection of the low level currents that are induced in the antenna by the dielectrokinesis effects of an unknown entity existing in the vicinity of the antenna. In particular, it is desirable to improve the distance in which the detector device can be accurately used to detect the unknown entity. That is, in detectors, increasing the distance that the detector device can unequivocally identify the presence of the entity is desirable. Unfortunately, as the distance between the detector and the detector entity increases, the signal strength received by detector due to the dielectrokinesis effects of the unknown entity are dramatically reduced and can thereby result in misidentifications of the presence of the entity. Since the current levels induced on antenna 102 can already be relatively low (at or below the JFET gating threshold), reductions in the current levels (and hence the signal to noise ratio) can have a dramatic impact on the operational characteristics including the maximum effective distance of detection.

In addition, the detector described with respect to Appendix A and B includes circuitry which is designed to sense the electric field in the vicinity of the detector caused by dielectrokinesis effects induced by the presence of the unknown entity. The detection occurs as a result of the induced current on the antenna 102 exceeding the gate threshold on the JFETs J1, J2, and J3. Current levels below the threshold will fail detection. This method can provide low sensitivity of operation since the operator will receive either a positive indication (via meter movement and piezo buzzing) if the current threshold is exceeded or no indication at all if it is not.

SUMMARY OF AN EXAMPLE EMBODIMENT OF THE INVENTION

The present metering circuit operates in conjunction with the antenna, filtering and detector circuit described in Appendix A and B. By replacing the JFETs of FIG. 5 of Appendix A with the present circuit, the operator can detect more subtle indications of the presence of an unknown entity.

With the present metering circuit, the operator sets the detection level to a particular value (preferably a null value) such that changes in the dielectrokinetic effects are more sensitively detected. Thus, for example, if ambient levels of electric field are 20 micro volts per cm and the change in field caused by the dielectrokinesis effect of introducing an unknown entity into the effective range of the antenna 102 causes a +1 micro volt per cm change in ambient conditions, the change from 20 to 21 on a meter might be indistinguishable to the JFET gates. In such a case, the meter and piezo buzzer would not adequately distinguish between an ambient condition and a changed condition.

If, however, the current detection circuit "zeros" itself at the ambient condition, the change from zero (ambient condition) to +1 micro volt per cm (when the unknown entity is introduced into the effective range of the antenna 102) can be more sensitively identified by the detection circuit and thereby provide a more obvious identification to the operator of the presence of an unknown entity.

The present invention thus advantageously provides improved sensitivity in detecting the presence of unidentified entities and also provides increased distances of effective operation.

BRIEF DESCRIPTION OF THE DRAWINGS

Other advantages and objects of the present invention will be described in detail with reference to the accompanying drawings, in which.

DETAILED DESCRIPTION OF THE PERSENTLY PREFERRED EMBODIMENTS

Figure 1:
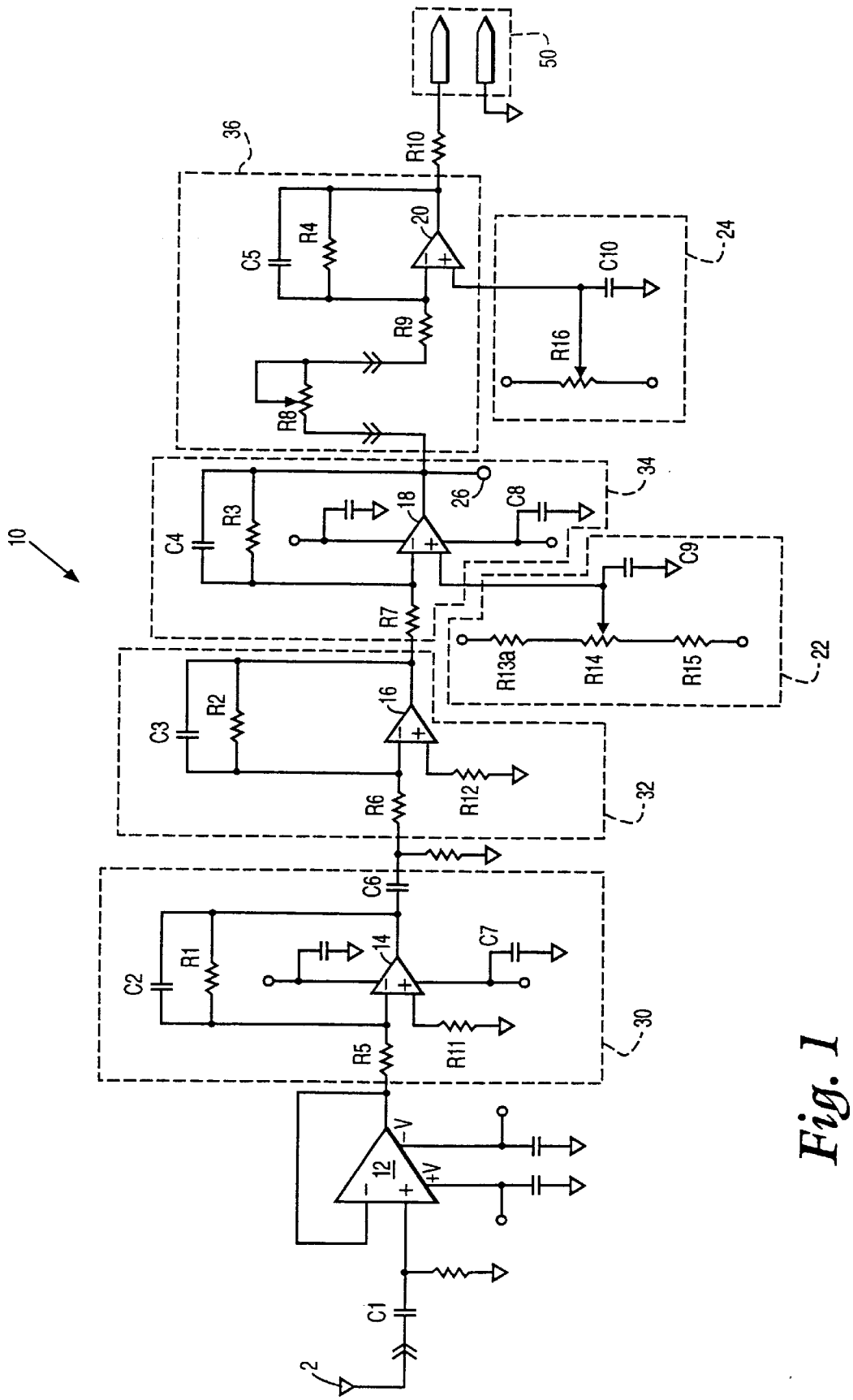
FIG. 1 is a circuit diagram of an example embodiment of the present invention.

FIG. 5 of Appendix A shows a circuit diagram in which an antenna 102 detects an electric field in the vicinity of the detector and delivers a low value current to a current detector circuit The present invention can be substituted into the apparatus described in Appendix A in connection with the same antenna 102 by substituting the circuit of FIG. 1 (attached) for the current detection circuit of FIG. 5 of Appendix A.

In this regard, FIG. 1 of the present invention illustrates an example embodiment of the improved current detector circuit 10. As shown in FIG. 1, the circuit 10 is connected to antenna 2 (coinciding with antenna 102 of FIG. 5 of Appendix A). The antenna 2 provides a low level current as electric fields are brought into effective proximity to it. The current detector circuit 10 senses the current provided by antenna 2 and provides an indication of that current to the operator via meter 50, in accordance with the purposes described with respect to U.S. application Ser. No. 08/758, 248.

The present current sensor 10 includes a series of amplifiers, beginning with a first operational amplifier 12 connected to a series of amplifier circuits 30, 32, 34, and 36. Operational amplifier 12 is preferably a low noise, low frequency precision Op amp that permits very low level input currents (on the pico amp level). An example operational amplifier suitable for the present current detector is marketed by Analog Devices of Norwood, Mass. under the product no. AD645, a data sheet corresponding to which is attached as Appendix C, which is incorporated herein by reference. Alternative amplifiers can be used provided they have a voltage noise spectral density curve to operate at a frequency at which the dielectrokinetic effects can be detected with sufficient sensitivity. For example, for detection of humans by detection of the dielectokinetic effects of the electrical signals in a human heart, an amplifier with a voltage noise spectral density curve to operate around 18 Hz or less, and preferably around 10 Hz, will suffice. Other— and different—operational characteristics may be more appropriate for detection of other types of entities or for detection of alternative physiological characteristics of human entities.

The frequency of operation for detecting a human depends upon the beat frequency of the heart. Typically, the beat frequency is around 1–2 Hz. By Fourier transforming the beat signal, one finds a fundamental frequency at about 17.5 Hz (hence the ideal operational characteristic of 18 Hz, or less). Of course, higher frequencies can be employed by focusing on the higher end components of the Fourier signal up to any frequency level for which the signal to noise ratio remains low enough to extrapolate a usable signal. The inventors have found that with present technology such higher and Fourier components can be employed up to about 50 Hz in Europe and 60 Hz in the U.S. before background noise overcomes the Fourier component signals.

The inverting input of the operational amplifier 12 receives a feedback signal from the output of OP amp 12. The non-inverting input of the operational amplifier 12 receives the antenna signal via series capacitor C1. C1 may be chosen based on the specific design constraints of the system used, but may preferably be a metal film capacitor of, for example, 0.47 $\mu$F.

The output of the operational amplifier 12 is then feed into the inverting input of amplifier 14 within first amplifier stage 30 via the resistor R5. Each of the amplifier stages 30, 32, 34, and 36 includes such a resistor (R5, R6, R7, and R8+R9) at the inverting input. In addition, the output of each of the amplifiers 14, 16, 18, and 20, of respectively, amplifier stages 30, 32, 34, and 36 is fed back to the inverting input of the respective amplifier via the parallel combination of corresponding resistors and capacitors R1, R2, R3, R4, and C2, C3, C4, and C5. Also at the output of amplifier 14 is coupling capacitor C6 which may be a 2.2. $\mu$F ceramic capacitor connected in series between the amplifier 14 and the second amplifier stage 32.

The non-inverting inputs of amplifiers 14 and 16 are tied to ground via resistors R11 and R12. For the non-inverting inputs of amplifiers 18 and 20 of amplifier stages 34 and 36, respectively, automatic nulling adjustments are provided. In particular, at the third amplifier stage 34, the non-inverting input of amplifier 18 is connected to variable resistor R14, which is connected in series to positive voltage (for example, +9 volts) through resistor R13 and is connected to minus voltage (for example, −9 volts) through resistor R15. The variable resistor R14 makes up a part of the zero offset adjustment circuit 22, which is connected to the non-inverting input of the amplifier 18.

Zero offset adjustment circuit 22 is provided to permit the operator to adjust the gain of the third stage to accommodate drift that may exist in the high gain amplifier stages. As an example embodiment of the zero adjust circuit 22, resistor R3 may have a value of 100K ohms, resistor R15 may have a value of 100K ohms and resistor R14 may have a value of 5K ohms. Further, capacitor C9 may have a value of 0.1 $\mu$F and may be a metal film capacitor.

The fourth amplifier stage 36 includes amplifier 20 and input resistors R8 in series with R9. Resistor R8 is variable and may have a value of 250K ohms, while resistor R9 is fixed at a value of 220K ohms. Resistor R8 is a potentiometer which provides a sensitivity adjustment for the operator. In addition, adjustment circuit 24 is provided into the non-inverting input of amplifier 20 to provide a center adjustment for the meter being used. This allows the operator to determine whether the presence of an unknown entity causes the metering circuit to build capacitance or to draw capacitance. Center adjustment circuit 24 includes variable resistor R16 connected between positive and negative voltage. It may be a 50K ohm resistor connected in parallel with capacitor C10 which may be a 0.1 microfarad metal film capacitor. Ideally, R16 is adjusted for half scale (i.e., centered on the meter) when no input signal is present.

The output of the fourth amplifier stage 36 is provided to a resistor R10 which may be 47K ohms, but will be adjusted depending upon the meter used. The output of the resistor R10 is provided to the meter 50 which will identify the presence of current at the antenna 2 to the operator, as amplified by the various amplifier stages discussed previously.

In operation, a very small current is detected in antenna 2 whenever the dielectrokinetic effects cause a change in electric field compared to ambient conditions. This current may be in the order of picoamps and is provided through blocking capacitor C1 to the non-inverting input of amplifier 12. This amplifier is frequency clipped at 10 Hz which is a preferred frequency at which tests show that the subtle dielectrokinesis effects of the presence of an unidentified entity are seen and coupling between the unidentified entity and the detector is maximized. The amplifier 12 increases the signal strength and provides the output to the four amplifier stages 30, 32, 34, and 36. These amplifier stages further boost the signal value such that the meter 50 at the output of the current detector circuit 10 can identify to a high degree of clarity the presence of an unidentified entity, even at larger distances such as, for example, 20 meters or more.

The circuit 10 will float to ambient electric field conditions such that, after, for example 2 to 3 seconds, the circuit nulls itself at the ambient condition. Thereafter, changes in the electric field caused by the dielectrokinetic effects of introducing another entity in the vicinity of the antenna 2 will be registered by the metering circuit. In this way, any changes to the ambient condition can be detected with greater sensitivity directly on the meter being used, as discussed above.

The present invention is not limited to the precise circuit shown in FIG. 1, but may employ other circuit designs which are low pass and keyed off of a device having a voltage noise spectral density curve to operate around 50 Hz or less, and preferably around 10–18 Hz. This allows the circuit 10 to sense a charge on the antenna 2 and use the charge to apply a series of gains for detection by a meter or other suitable device.

The present invention has many uses and is not necessarily limited to any particular use. The inventors have found that the antenna detector and metering circuit can be used to detect the presence of hidden entities, including humans, animals, polymers, controlled substances, etc. Further applications include the detection of movement (motion detectors) in a defined environment. For example, when an entity is perfectly still within a room, the present circuit will first detect the entity, then (after a few seconds) null itself to the ambient condition. Thereafter, if the entity moves, the meter will register changes in the dielectrokinetic effect in the room caused by the change in physical orientation of the human's heart relative to the detecting antenna 2 (which in turn changes the electric field sensed by the antenna 2).

Another application of the invention is within the medical diagnostic field. In particular, the invention can be used to numerically characterize the electric field associated with a human heart muscle and the conductive nerves. This permits the operator to view these electric field characteristics against a norm to provide an indication of health of the heart. One possible characteristic (of potentially many different characteristics) that can be detected is the heart rate variability and the synchronization between the sympathetic and parasympathetic rhythms. In this regard, the present invention is more sensitive in detecting heart condition than, for example, prior art ECG tests.

A further alternative use of the invention is operation in an autonomous mode, without the presence of a "reference entity" (such as a human operator) in contact with the ground plane GP1, as shown in FIG. 5 of Appendix A and described at page 12 of Appendix A. The inventors have found that, by choosing the proper operating characteristics of the amplifier 12 (as described above and in the example of Appendix C), the detection and metering circuits will operate without a reference entity in physical connection with the ground plane. This permits the device to operate as a stand-alone device, without the need for a physically present operator.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

What is claimed is:

1. An apparatus to detect a change in dielectrokinesis effects in an environment characterized at any instant by an instantaneous ambient dielectrokinetic condition, comprising:

a current detector for electrical connection to an antenna to receive from the antenna an antenna signal indicative of said change in dielectrokinesis effects, comprising:

a low input current amplifier having a voltage noise spectral density curve to operate at 50 Hz or less and connected to receive the antenna signal and to output a first signal, and an amplifier stage connected in series with the low input current amplifier to amplify the first signal into an output signal for use by a detection device to identify the change in dielectrokinesis effects, wherein the amplifier stage includes a zeroing circuit to periodically standardize the output signal to a predetermined value commensurate with the instantaneous ambient dielectrokinetic condition.

2. An apparatus according to claim 1, wherein the antenna signal is low frequency and low current at the low input current amplifier.

3. An apparatus according to claim 1, wherein the low current amplifier is an operational amplifier having a voltage noise spectral density curve to operate under 18 Hz.

4. An apparatus according to claim 1, wherein the low input current amplifier is clipped at 10 Hz or less.

5. An apparatus according to claim 1, wherein the low input current amplifier is a feedback operational amplifier.

6. An apparatus according to claim 1, wherein the amplifier stage includes a series of amplifiers.

7. An apparatus according to claim 6, wherein the series of amplifiers includes first through third amplifier stages, the first amplifier stage being a fixed gain amplifier, the second amplifier stage being a variable gain amplifier that varies according to a zero offset adjustment, and the third amplifier stage being a variable gain amplifier that varies according to a center adjustment.

8. An apparatus according to claim 7, wherein the second amplifier stage includes a voltage divider circuit to provide said zero offset adjustment.

9. An apparatus according to claim 7, wherein the third amplifier stage includes a voltage divider circuit to provide said center adjustment.

10. An apparatus according to claim 7, further including a potentiometer between said second and third amplifier stages.

11. An apparatus according to claim 7, wherein the first through third amplifier stages are connected in consecutive series.

12. An apparatus according to claim 7, further including a fourth amplifier stage.

13. An apparatus according to claim 1, wherein the zeroing circuit periodically standardizes the output signal to a null value.

14. An apparatus according to claim 1, wherein the antenna employs the dielectrokinesis effects of a human operator.

15. An apparatus according to claim 1, wherein the antenna does not employ the dielectrokinesis effects of a human operator.

16. A method of detecting a change in dielectrokinesis effects in an environment characterized at any instant by an instantaneous ambient dielectrokinetic condition, comprising the steps of:

receiving, from an antenna, an antenna signal indicative of said change in dielectrokinesis effects, first amplifying the antenna signal by a low input current amplifier having a voltage noise spectral density curve to operate under 50 Hz and outputting the resultant signal as a first signal, and second amplifying the first signal into an output signal for use by a detection device to identify the change in dielectrokinesis effects, including the step of:
periodically standardizing the output signal to a predetermined value commensurate with the instantaneous ambient dielectrokinetic condition.

17. A method according to claim 16, wherein the first amplifying step includes the step of amplifying at a low frequency.

18. A method according to claim 16, wherein the step of first amplifying includes the step of amplifying using an operational amplifier having a voltage noise spectral density curve to operate under 18 Hz.

19. A method according to claim 16, wherein the step of first amplifying includes the step of amplifying using an amplifier clipped at 10 Hz or less.

20. A method according to claim 16, wherein the step of first amplifying includes the step of feeding back the first signal.

21. A method according to claim 16, wherein the step of second amplifying includes the step of amplifying through a series of amplifiers.

22. A method according to claim 21, wherein the step of second amplifying includes the steps of amplifying through first through third amplifier stages, and wherein:
the first amplifier stage provides a fixed gain,
the second amplifier stage provides a variable gain that varies according to a zero offset adjustment, and
the third amplifier stage provides a variable gain that varies according to a center adjustment.

23. A method according to claim 22, wherein the second amplifier stage provides a voltage divider circuit to provide said zero offset adjustment.

24. A method according to claim 22, wherein the third amplifier stage provides a voltage divider circuit to provide said center adjustment.

25. A method according to claim 22, further including the step of adjusting the further including a potentiometer between said second and third amplifier stages.

26. A method according to claim 22, wherein the step of second amplifying includes the step of amplifying through a fourth amplifier stage.

27. A method according to claim 16, wherein the step of periodically standardizing includes standardizing the output signal to a null value.

28. A method comprising the steps of:
diagnosing a physiological condition of a human using an apparatus to detect a change in dielectrokinesis effects in an environment characterized at any instant by an instantaneous ambient dielectrokinetic condition, comprising:
a current detector for electrical connection to an antenna to receive from the antenna an antenna signal indicative of said change in dielectrokinesis effects, comprising:
a low input current amplifier having a voltage noise spectral density curve to operate at 50 Hz or less and connected to receive the antenna signal and to output a first signal, and
an amplifier stage connected in series with the low input current amplifier to amplify the first signal into an output signal for use by a detection device to identify the change in dielectrokinesis effects, wherein the amplifier stage includes a zeroing circuit to periodically standardize the output signal to a predetermined value commensurate with the instantaneous ambient dielectrokinetic condition.

* * * * *